United States Patent [19]
Seidel et al.

[11] 3,962,420
[45] June 8, 1976

[54] DISSOLUTION OF GALLSTONES

[75] Inventors: Michael C. Seidel, Chalfont, Pa.; Evan H. Crook, Cherry Hill, N.J.

[73] Assignee: Rohm and Haas Company, Philadelphia, Pa.

[22] Filed: July 3, 1974

[21] Appl. No.: 485,476

[52] U.S. Cl. ............................ 424/81; 424/78; 424/83
[51] Int. Cl.² ................................. A61K 31/78
[58] Field of Search .................... 424/78, 81, 83

[56] References Cited
UNITED STATES PATENTS

| | | |
|---|---|---|
| 3,308,020 | 3/1967 | Wolf et al. ........................ 424/78 |
| 3,649,456 | 3/1972 | Benneville et al. ................ 195/66 |
| 3,663,467 | 5/1972 | Albright ............................ 260/2.5 |
| 3,787,474 | 1/1974 | Daniels et al. .................... 260/459 |
| 3,794,584 | 2/1974 | Kunin ............................... 210/24 |

*Primary Examiner*—Frederick E. Waddell
*Attorney, Agent, or Firm*—Terence P. Strobaugh; George W. F. Simmons; Carl A. Castellan

[57] ABSTRACT

Macroreticular resins have shown biological activity for gallstone removal and lowering serum cholesterol by selective adsorption of cholesterol from the bile.

9 Claims, No Drawings

DISSOLUTION OF GALLSTONES

The present invention relates to the use of macroreticular resins for dissolution of cholesterol gallstones, and the lowering of serum cholesterol. In particular, the invention concerns the use of nonpolar or slightly polar macroreticular resinous adsorbents for dissolving cholesterol gallstones.

Pharmacological studies show that the use of an effective amount of nonpolar or slightly polar adsorbent macroreticular resins causes a decrease in cholesterol which results in the dissolution of cholesterol gallstones and also a reduction of serum cholesterol. When administered in therapeutic dosages in conventional pharmaceutically acceptable vehicles, the macroreticular resins lower serum cholesterol and provide a convenient means for the non-surgical removal of gallstones.

The term "gallstone" is described in Dorland's Medical Dictionary as "a concretion, usually of cholesterol, formed in the gallbladder or bile duct". The medical term describing this disease is cholelithiasis. Cholelithiasis is one of the most prevalent diseases in Western Civilization. If is estimated that 15 million people in the United States have gallstones, and that approximately 800,000 new cases occur each year. At present, the removal of gallstones is done surgically. Cholesterol is widely distributed throughout the body, both free and as cholesterol esters and is derived from three main sources. The liver and small intestine synthesize cholesterol (endogenous). A total of 1 to 3 grams is delivered daily from all sources, (including food) by way of the intestinal tract to the lymph.

The cholesterol synthesized in the liver can be excreted into the bile, degraded to bile acids, or exchanged with the cholesterol pool outside of the liver. Hepatic, plasma and biliary cholesterol are reported to be in rapidly achieved equilibrium but there is some doubt that this is true. The mean pool size for man is 28 grams; ⅔ of plasma cholesterol and 4/5 liver cholesterol is esterified, while 95% of the cholesterol in bile is not esterified.

The bile produced by the liver is stored and concentrated by the gallbladder. During this process, the volume is reduced by the adsorption of an isotonic NaCl-HCO₃⁻ solution. The normal gallbladder mucous membrane is impermeable to conjugated bilirubin, cholesterol, and bile salts and the concentration of these substances increases 5 to 10 fold.

The normal composition of the hepatic and gallbladder bile in man is as follows:

| Constituent | Hepatic Bile mg/ml | Hepatic Bile mean% | Gallbladder Bile mg/ml | Gallbladder Bile mean% |
|---|---|---|---|---|
| Total solids | 25–50 | | 150–300 | |
| Bile salts | 12–20 | 60 | 70–150 | 60 |
| Phospholipids (96% lecithin) | 4–8 | 20 | 25–60 | 20 |
| Cholesterol | 1–2 | 5 | 5–15 | 5 |
| Bilirubin | 1 | 2 | 3–7 | 2 |
| Protein | 0–0.5 | 1 | 3 | 1 |
| Electrolytes | 7–8 | 15 | 7–8 | 3 |

The primary human bile acids are salts of cholic and chenodeoxycholic acid. They are formed in equal amounts by the liver from cholesterol and excreted into the bile as conjugates of glycine or taurine. Normally, free bile acids are not found in the bile. The normal bile salt pool in man is 3 to 5 grams with the primary bile acids comprising 80%. The remainder, or secondary bile salts, are derived from the primary bile salts which have undergone bacterial 7-dehydroxylation in the gut.

The phospholipids are also synthesized exclusively in the liver. The estimated hepatic pool in man is 25 to 30 grams. Lecithin is the major phospholipid in bile (> 90%). The other biliary phospholipids are lysolecithin (3%) and phosphatidyl ethanolamine (1%).

Bilirubin is present in bile as the conjugated, water soluble diglucuronides. This can be hydrolyzed by $\beta$-glucuronidase. However, no enzyme activity has been reported in normal bile, which is said to contain a powerful inhibitor, glucaro-1,4-lactone.

Lecithin and cholesterol are the only components which are not freely soluble in water. However, when lecithin is mixed with bile salts which have detergent properties, they form mixed micelles which solubilize cholesterol. The maximal cholesterol solubilization capacity is found at a bile acid/lecithin ratio of about 2. In normal bile, the micelles are saturated with cholesterol to 75–90%. Therefore, even a small change in the bile acid-lecithin/cholesterol ratio may result in cholesterol precipitation.

When the limits of micellar solubilization are surpassed, cholesterol remains in the supersaturated state. This condition is described as lithogenic bile. It has been shown that, in general, gallstone patients do have a reduced bile acid pool and a reduced ratio of bile acid-lecithin to cholesterol in hepatic as well as gallbladder bile.

A device used in determining the lithogenicity of bile is the lipid composition phase diagram. It measures the mole percent of cholesterol, bile salts and lecithin found in bile.

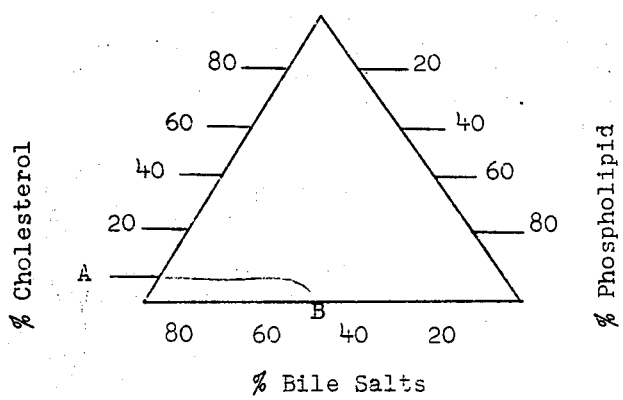

Liquid Composition Phase Diagram

The triangle represents the three component system. The hatched area shows those mixtures forming one liquid (micellar) phase. Line AB indicates the maximum solubility of cholesterol.

Some of the biochemical factors that have been found to be the causes of lithogenic bile are:

1. A reduction in hepatic conjugating activity. Some of the bile acids are deconjugated by bacteria in the gut. If the recycling free bile acids are not reconjugated, the cholesterol-binding capacity is reduced.
2. Cholesterol esterified with polyunsaturated fatty acids, especially arachidonic acid, is an important precursor of bile acids. Thus a disturbance in the metabolism of linoleic acid, the main fatty acid precursor of aracidonic acid, can depress bile salt synthesis.
3. It has been shown that injections of fructose causes significant decreases in phospholipid synthesis in the liver. Thus a decreased synthesis of lecithin may explain the increased incidence of gallstones when the diet contains very high amounts of sucrose.
4. A high caloric intake causes increased hepatic cholesterogenesis. This seems to occur regardless of dietary composition.

Some of the physiological factors which have been found to cause lithogenic bile are:

1. Altered gallbladder emptying.
2. Bacterial infection of the bile causing deconjugation of bile acids.
3. A decreased bile salt pool relative to the amount of cholesterol excreted into the bile.

It appears that many factors contribute to the precipitation of cholesterol in bile and it is possible that many of these factors are cooperating in the formation process and in the further development of gallstones.

The traditional classification of gallstones into cholesterol, pigment, and mixed types is now recognized as an oversimplification. Analysis of biliary calculi by a variety of methods, including IR, GLC and X-ray diffraction has shown that the composition of human gallstone is complex. The major constituents are cholesterol, monohydrate calcium carbonate and calcium bilirubinate. Cholesterol is the predominant constituent in 85% of gallstones in man, but most calculi contain all three substances. Many other substances may be present in smaller amounts including bile salts, proteins, fatty acids, mucopolysaccharides, P, Fe, Cu, and manganese.

It has been found that by employing adsorbent macroreticular resins intestinal cholesterol is selectively adsorbed from the GI tract without affecting bile acid readsorption which results in a disturbance of the bile acid/cholesterol ratio causing reduced lithogenicity which results in the dissolution of cholesterol gallstones.

The macroreticular resins employed as the adsorbents herein are not new compositions. Any of the nonpolar or slightly polar known materials of this type are suitable.

The polarity of the adsorbent macroreticular resins involves many types of interaction such as hydrophobic bonding, dipole-dipole interaction and hydrogen bonding. The resins prepared from aromatic ethylenically unsaturated monomers are nonpolar resins, those resins prepared from aliphatic ethylenically unsaturated monomers are slightly polar whereas resins prepared from both aromatic and aliphatic ethylenically unsaturated monomers are of intermediate polarity and include those resins disclosed in U.S. Pat. No. 3,663,467, British Pat. Nos. 932,125 and 932,126 which patents are hereby incorporated by reference. For example, there may be used granular cross-linked polymers containing from 2 to 100 percent by weight of units of one or more polyethylenically unsaturated monomers prepared by suspension polymerization of aromatic ethylenically unsaturated monomers comprising from 2 to 100 weight percent of one or more mono or poly(vinyl)benzene monomers such as styrene, divinylbenzene, trivinylbenzene and the like, mono- or divinylalkyl substituted or trivinylalkyl substituted benzene wherein the benzene nucleus is substituted with from 1–4 alkyl groups including lower alkyls of from 1–2 carbon atoms such as methyl ethyl and the like. The homopolymers and copolymers of these mono- or poly(vinyl)benzene monomers may be copolymerized with up to 98 percent (by weight of the total monomer mixture) of (1) monoethylenically unsaturated monomers or (2) polyethylenically unsaturated monomers other than the poly(vinyl)benzenes just defined or (3) a mixture of (1) and (2) and still result in a suitable macroreticular resin. In order to produce the high porosity and high specific surface areas required of the resins in the present invention, suspension polymerization procedures well known in the art may be employed, for example, the procedures disclosed in the three patents mentioned above.

Examples of mono-, di- and trivinylalkyl substituted benzene monomers include ethylvinylbenzene, vinyltoluenes, divinylxylenes, divinylethylbenzenes, 1,4-divinyl-2,3,5,6-tetramethylbenzene, 1,3,5-trivinyl-2,4,6-trimethylbenzene, 1,4-divinyl,2,3,6-triethylbenzene, 1,2,4-trivinyl-3,5-diethylbenzene, 1,3,5-trivinyl-2-methylbenzene and the like.

Examples of monoethylenically unsaturated monomers referred to above include the acrylate and methacrylate esters such as the methyl, ethyl, propyl, isopropyl, butyl, tertbutyl, ethylhexyl, cyclohexyl, isobornyl, benzyl, phenyl, alkylphenyl, ethoxymethyl, ethoxyethyl, ethoxypropyl, propoxymethyl, propoxyethyl, propoxypropyl, ethoxyphenyl, ethoxybenzyl, ethoxycyclohexyl acrylates and methacrylates, also included are ethylene, propylene, isobutylene, diisobutylene, vinyl chloride, vinyl acetate, vinylidene chloride, acrylonitrile and the like. Polyethylenically unsaturated monomers which contain only one polymerizable ethylenically unsaturated group, such as isoprene, butadiene and chloroprene, are also to be regarded as falling within the category of monoethylenically unsaturated monomers. Examples of polyethylenically unsaturated monomers referred to above include divinylpyridine, divinylnaphthalenes, diallyl phthalate, ethylene glycol diacrylate, ethylene glycol dimethacrylate, divinylsulfone, polyvinyl or polyallyl ethers or glycol, glycerol or pentaerylthritol, monothio-or dithio-derivatives of glycols or resorcinol, divinylketone, divinylsulfide, allyl acrylate, diallyl maleate, diallyl fumarate, diallyl succinate, diallyl carbonate, diallyl malonate, diallyl oxalate, diallyl adipate, diallyl sebacate, divinyl sebacate, diallyl tartrate, diallyl silicate, triallyl tricarballylate, triallyl aconitate, triallyl citrate, triallyl phosphate, N,N'-methylenedimethacrylamide, N,N'-ethylenediacrylamide, trivinylnaphthalenes, polyvinylanthracenes and the like. Alternatively, the macroreticular crosslinked polymer may comprise essentially all aliphatic materials, for example, it may comprise 2–100 percent by weight of an acrylic or methacrylic ester such as trimethylolpropane trimethacrylate and the like, the balance preferably comprising another polar monomer such as an acrylate of the type mentioned above, acrylonitrile and the like.

The preferred resins are those having the following structure;

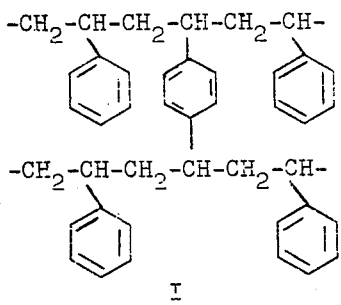

I

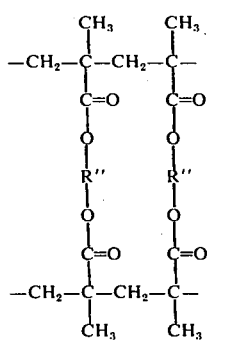

II

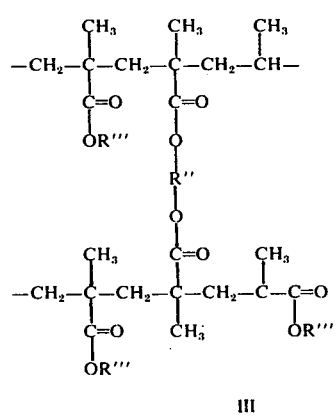

III

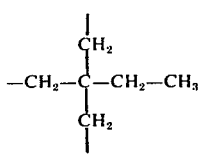

wherein R'' in formula II and III is and R''' is lower alkyl, for example, methyl, ethyl, and the like. Resins of these structures are preferred because they exhibit particularly good gallstone dissolution.

The preferred proportion of the polyethylenically unsaturated crosslinking monomer is from 8 to 25 percent by weight of the total monomer mixture from which the resin is prepared. Suspension polymerization usually produces the resin in the form of granules or beads having an overall bead size in the range of about 0.1 to about 3 millimeters average diameter. The bead form of the resin is quite useful for the adsorption process of the invention. In this process the material or substance being separated or concentrated is adsorbed on the surface of the resin particles and the effectiveness of the process depends on the presence of a high ratio of surface area to weight of resin.

The macroreticular beads vary in diameter over a wide range, and are separated by conventional screening techniques. For the instant invention, it is desirable to have the particles of resin as small as possible. One can adjust the amount or type of surfactant and the stirring rate during the polymerization, to prepare macroreticular beads in the 140 to 325 mesh, or smaller, which will perform satisfactorily without further comminution in the adsorbing and excreting of cholesterol.

Beads of any size may be crushed and ground to a fine powder, preferably 100 microns or less. The macroreticular structure of the polymeric material is maintained when it is crushed, and thus a high surface area is immediately available on which the cholesterol is adsorbed. It is not possible with conventional equipment to comminute the conventional gel resins to give a comparable surface area.

The macroreticular resin used in the process of the invention should be in the range of from $0.1\mu$ to $300\mu$ (50 mesh, U.S. Standard Screen Series) and preferably in the range of from $1\mu$ to $45\mu$ (smaller than 325 mesh, U.S. Standard Screen Series).

Macroreticular resins are characterized by the presence throughout the polymeric matrix of a network of "extra-gellular" micro channels or pores. While these micro channels are very small, they are large in comparison with the pores in conventional homogeneous crosslinked gels. Macroreticular resins suitable for use in the invention may have specific surface areas of up to 2,000 sq. m. per gram or more.

The preferred resins are crosslinked resins which have solubility parameters (expressed in the units $$\sqrt{\frac{\text{Calories}}{\text{cubic centimeter}}}$$

of at least 8.5 and those having such parameters up to 15 or more are satisfactory for use in aqueous systems. The substantially non-ionogenic macroreticular crosslinked synthetic resin has a porosity of at least 10 percent, a specific surface area of at least 10 sq. m. per gram and which is not appreciably swollen by the medium, so that the substance is adsorbed on to the surface of the resin, the substance being then, if desired, desorbed from the resin. Preferably the macroreticular absorbent resin will have a surface area in the range of about 50 to 1,000 sq. meters per gram with a more preferred range being about 100 to 500 sq. meters per gram. The average pore diameter is also of some significance and it should range of from about 50 A. to about 1,000 A., and more preferably from about 75 A. to about 400 A. The physical properties of the macroreticular adsorbent resins, for example, porosity, surface area, pore size, etc., may be determined in accordance with standard techniques practiced in the art; for example, see pp. 153–167 of the book entitled *Oxidation-Reduction Polymers* by Cassidy and Kun, copyright 1965, published by Interscience Publications, New York, New York.

The following examples represent the preparation of some of the known macroreticular resins and the preparation of various dosage forms. However, the examples are illustrative only and it will be apparent to those having ordinary skill in the art that other macroreticular resins can be formulated in a similar manner.

EXAMPLE I — AROMATIC MACRORETICULAR RESIN

A mixture of styrene (35 g.), technical divinylbenzene (35 g.), deodorized kerosene (104 g.), toluene (55 g.), and benzoyl peroxide (1.5 g.) is added to a solution of sodium chloride (8.8 g.), Amberlite W-1 (5.1 g. ammonium salt of styrene/maleic anhydride copolymer), sodium bicarbonate (1.4 g.), and gelatin (0.06 g.) in water (250 g.). The mixture is agitated until the organic phase is dispersed as fine droplets and then heated at 80° C. for five hours. The mixture of liquids is removed from the resulting polymer pearls, which are then washed copiously with methanol until addition of the wash to water shows no turbidity. They are then air-dried to afford 59 g. of white, opaque spherical beads. The beads are then screened to afford suitable mesh sizes in the range of 20–100 mesh.

EXAMPLE II — AROMATIC MACRORETICULAR RESIN

The following oil phase and water phase mixtures are made up and added to a three-liter flask.

| (a) Oil Phase: | Divinylbenzene redistilled tech. (60% divinylbenzene 40% ethylstyrene) | 122.5 g. |
|---|---|---|
| | Styrene | 122.5 g. |
| | Deodorized kerosene | 364 g. |
| | o-Dichlorobenzene | 361 g. |
| | Benzoyl peroxide | 5.25 g. |
| (b) Water Phase: | Deionized water | 875 ml. |
| | Sodium chloride | 30.8 g. |
| | Sodium bicarbonate | 4.9 g. |
| | Amberlite W-1 | 17.85 g. |
| | Gelatin (Knox edible) | 0.21 g. |

A blade stirrer is used at 175 rpm. The mixture is brought to a uniform suspension and heated for 16 hours at 80° C. The resulting polymer beads are washed successively with deionized water (4 × 1 liter), ethanol (3 × 1 liter) (denatured 2B) and toluene (3 × 1 liter). The beads are transferred into a chromotographic column and washed with methanol until free of toluene. The excess methanol is removed and the beads refluxed with a solution of KOH (50 g.) in ethanol (1.4 liter) for 7 hours. The beads are washed free of KOH with ethanol and air dried to afford 237 g. of resin.

EXAMPLE III — ALIPHATIC RESINS

A homogeneous solution is prepared in a 12 l. flask from water (6000 g.), sodium chloride (18 g.), gelatin (6 g.) and an aqueous solution of sodium polyacrylate (72 g.; 12.5 wt. %). The pH of the solution is adjusted to 8–9 with concentrated aqueous ammonia. A mixture of commercial trimethylolpropane trimethacrylate (900 g.), lauroyl peroxide (9 g.) and toluene (2100 g.) is introduced into the reactor. The dispersion of organic liquid in an aqueous phase is prepared at ambient temperature at 80 rpm with on-off agitation cycles until only droplet and aqueous phases remain in the absence of stirring. Formation of the dispersion requires approximately fifteen minutes. The droplets are polymerized under nitrogen at 65° C. for 20 hours. The solid opaque spheres obtained are washed and dried to afford 896 g. (99.5% yield) of resin.

The following aliphatic resins are prepared following substantially the procedure of Example III except for the indicated changes in monomers and solvents.

| Ex. No. | Composition | | Solvent |
|---|---|---|---|
| 4 | TMPTMA[a] | 92% | Toluene |
| | TMPDMA[b] | 8% | |
| 5 | TMPTMA | 46.5% | MIBC[g] |
| | TMPDMA | 3.5% | |
| | MMA[c] | 50% | |
| 6 | MA[d] | 50% | MIBC |
| | TMPTMA[e] | 46.5% | |
| | TMPDMA | 3.5% | |
| 7 | PETMA[e] | 75% | Xylene |
| | PEtriMA | 25%[f] | | a — trimethylolpropane trimethacrylate; b — trimethylolpropane dimethacrylate; c — methyl methacrylate; d — methyl acrylate; e — pentaerythritol tetramethacrylate; f — pentaerythritol trimethacrylate and g — methylisobutyl carbinol.

EXAMPLE VIII — MACRORETICULAR DIVINYL BENZENE/METHACRYLATE RESIN

To a one liter three neck round bottom flask is added 337 g. water (33 g.), Pharmagel (0.7 g.) (a commercial low molecular weight protein), boric acid (1.05 g.), sodium chloride (3.5 g.) and Padmac (7.7 g.) (a cyclo polymer of dimethyl diallyl ammonium chloride). The pH is adjusted to 10–10.5 using sodium hydroxide. To this is added divinyl benzene (78.5 g.), trimethylol propane trimethacrylate (26.25 g.), benzoyl peroxide (0.9 g.) and toluene (245 g.). The two phases are emulsified and heated to 80° C. over a 1½ hour period under nitrogen with stirring at 200 rpm. The organic phase is then removed by azeotroping. The beads obtained are washed with methanol and water. Finally, the resin beads are dried to about 40% water, ground and sieved to desired particle size.

EXAMPLE IX — MACRORETICULAR METHACRYLATE RESIN

By following substantially the procedure in Example VIII and by substituting for the divinyl benzene and trimethylol propane trimethacrylate recited therein a single charge of trimethylol propane trimethacrylate (105 g.) a slightly polar macroreticular methacrylate resin is prepared. The hard, hydrated beads have an average particle size of 0.3 to 0.45 mm. The dried beads have a porosity of 0.5 to 0.55 mm. of pore /ml. of bead.

EXAMPLE X — Macroreticular Divinylbenzene Resin

By following substantially the procedure in Example VIII and by employing divinylbenzene (105 g.) in place of the divinyl benzene and trimethylol propane trimethacrylate recited therein, there is obtained a nonpolar macroreticular divinyl benzene resin as hard, hydrated opaque beads.

The macroreticular resins can be administered in a wide variety of therapeutic dosages in conventional vehicles, for example, by oral administration in the form of a tablet. Also, the daily dosage of the products may be varied over a wide range varying from 1 to 15 grams and preferably in the range of 5–10 grams. The product is conveniently administered in subdivided dosages of 500, 1000, 2000 or more milligrams of the active ingredients for the symptomatic adjustment of the dosage to the patient to be treated.

Compressed tablets, pills, wafers, powders, suspensions or other desired unit dosages can be prepared to incorporate the compounds of this invention by conventional methods and well known to pharmacists.

Exemplary of solid carriers are lactose, terra alba, sucrose, talc, gelatin, agar, pecting, acacia, magnesium stearate, stearic acid and the like. Exemplary of liquid carriers are syrup, peanut oil, olive oil, water and the like. Similarly, the carrier or diluent include any time delay material well known to the art, such as glyceryl disstearate, alone, or with a wax.

These preparations are made following the conventional techniques of the pharmaceutical chemist involving mixing, granulating and compressing when necessary, or variously mixing and dissolving the ingredients as appropriate to the desired end product.

It is also within the scope of this invention to combine two or more of the compounds of this invention in a unit dosage form or to combine one or more of the compounds of this invention with other desired therapuetic and/or nutrative agents in a dosage unit form.

The following examples illustrate the preparation of a representative dosage forms:

EXAMPLE XI - TABLETS CONTAINING 500 MG. OF ACTIVE INGREDIENT PER TABLET

I. Tablet

| | | |
|---|---|---|
| Resin of Example IX | 500.0 | mg. |
| Starch, USP (Paste) | 75.0 | mg. |
| Starch, USP | 25.0 | mg. |
| Magnesium Stearate | 5.0 | mg. |
| | 605.0 | mg. |

The resin of Example IX is passed through a mill to reduce the particle size such as it passes through a number 40 mesh screen. To this resin is added a starch base prepared with boiling water. The combined ingredients are thoroughly mixed and, if required, additional purification may be added to prepare a suitable granulation. The wet granulation mixture is passed through an oscillating granulator and dried to the desired moisture content. The dried granulation is then passed through a screen and the remainder of the starchmagnesium stearate is added and the combined ingredients are remixed. After remixing, the ingredients are compressed into 605 mg. tablets using a Stoke's Model B-2 rotary table press.

EXAMPLE XII — TABLET CONTAINING 500 MG. OF ACTIVE INGREDIENT

| | |
|---|---|
| Resin of Example IX | 500 mg. |
| Microcrystalline Cellulose, NF* | 50 mg. |
| Lactose, Anhydrous | 50 mg. |
| Calcium Stearate | 5 mg. |
| | 605 mg. |

*Avicel PH101 (trade name) FMC Corporation

The ingredients are combined and passed through No. 40 mesh screen and then blended together. After blending, the ingredients are compressed into 605 mg. tablets on a Stoke's Model B-2 rotary tablet press.

EXAMPLE XIII — PREPARATION OF A POWDER

| | per 100 gm | per 4 gm |
|---|---|---|
| Resin of Example 1 | 50.0 mg. | 2.000 gm |
| Lactose, USP | 49.9 mg | 1.996 gm |
| Fumed Silica* | 0.1 mg | 0.004 gm |

*Trade name Cab-O-Sil, M-5, Cabot Corporation

The ingredients are mixed and passed through a No. 40 mesh screen and then blended thoroughly to obtain a uniform mixture. The powder is packaged into a 4 gm packet using a laminated polyethylene, foil, paper pouch on a suitable form, fill and seal machine.

EXAMPLE XIV — HARD GELATIN CAPSULE

| | |
|---|---|
| Resin of Example I | 400 mg. |
| Magnesium Stearate | 3.6 mg. |
| Fumed Silica* | 0.4 mg. |

*Trade name Cab-O-Sil, M-5 Cabot Corporation

The ingredients are combined and passed through a No. 40 mesh screen and then the powder blended thoroughly to obtain a uniform mixture. The thoroughly mixed ingredients are then filled into a No. 00 hard gelatin capsule.

EXAMPLE XV — SUSPENSION

| | |
|---|---|
| Resin of Example II | 20.0% |
| Glycerin | 10.0% |
| Syrup | 30.0% |
| Sodium Carboxymethyl Cellulose | 0.25% |
| Water, purified | q.s. |

The sodium carboxymethyl cellulose is added to the glycerin and the mixture thoroughly stirred till free of lumps. This mixture is then added to water with vigorous agitation till a clear solution is formed at which time the syrup is added. To this liquid is added the resin of Example II which has been passed through a suitable No. 100 mesh screen. After thorough mixing, the suspension is passed through a No. 60 mesh screen.

EXAMPLE XVI - SUSPENSION

| | |
|---|---|
| Resin of Example IX | 20% |
| Glycerin | 1.0% |
| Tragacanth, USP | 0.5% |
| Triton Surfactant 1339 | 0.2% |
| Antifoam | 60 ppm |
| Water, purified | q.s. |
| Benzoic Acid | 0.1% |

To a mixture of glycerin and ½ of the total volume of water which has been heated to boiling, is added tragacanth and benzoic acid. The resulting mixture is macerated for 24 hours after which time there is added the remainder of the water, Triton 1339, and antifoam and then the mixture is strained through a No. 100 mesh screen. To this mixture is added the resin of Example IX which has been passed through a No. 100 mesh screen. The suspension is passed through a No. 60 mesh screen and remixed.

EXAMPLE XVII - SUSPENSION

| | |
|---|---|
| Resin of Example VIII | 20% |
| Syrup | 70% |
| Veegum | 1% |
| Water, purified | q.s. |

To a mixture of the veegum and water which has been heated and subsequently cooled below 40° C., is added the syrup. The resin of Example VIII is passed through a No. 100 mesh screen and added directly to the suspending vehicle after which the product is passed through a No. 60 mesh screen and then remixed.

It will be apparent from the foregoing description that other therapeutic dosages can be formulated. One skilled in the art will appreciate that the dosage form Examples disclosed above are merely illustrative and are capable of wide variation and modification without departing from the spirit of this invention

What is claimed is:

1. A method for causing the dissolution of cholesterol gallstones and lowering of serum cholesterol which comprises the oral administration of an effective amount of an adsorbent macroreticular resin having a particle size of from $0.1\mu$ to $300\mu$ comprising aromatic ethylenically unsaturated monomers, aliphatic ethylenically unsaturated monomers or mixtures thereof wherein said resin selectively adsorbs cholesterol from the GI tract without affecting bile acid readsorption resulting in a disturbance of the bile acid to cholesterol ratio causing reduced lithogenicity.

2. The method of claim 1, wherein the adsorbent macroreticular resin is prepared by suspension polymerization.

3. The method of claim 2, wherein the macroreticular resin is prepared from 2 to 100 weight percent of one or more mono- or poly(vinyl)benzene monomers, divinyl alkyl substituted benzene, trivinyl alkyl substituted benzene or an acrylic or methacrylic ester.

4. The method of claim 3, wherein the macroreticular resin comprises one or more mono- or poly(vinyl)benzene monomer selected from styrene, divinylbenzene, trivinylbenzene or mixtures thereof; mono- or divinylalkyl substituted benzene or trivinylalkyl substituted benzene monomer selected from ethylvinylbenzene, vinyl toluene, divinylethylbenzene or mixtures thereof and an acrylic or methacrylic ester.

5. The method of claim 4, wherein the macroreticular resin comprises 100% by weight of an acrylic or methacrylic ester.

6. The method of claim 4 wherein the macroreticular resin comprises 100% by weight of a copolymer of divinylbenzene and ethylvinylbenzene.

7. The method of claim 4 wherein the macroreticular resin is comprised of a copolymer of divinylbenzene and styrene.

8. The method of claim 4 comprising a macroreticular resin of a copolymer of divinylbenzene and trimethylolpropane trimethacrylate.

9. The method of claim 5, wherein the ester is trimethylolpropane dimethacrylate, trimethylolpropane trimethacrylate or methyl methacrylate.

* * * * *

UNITED STATES PATENT OFFICE
CERTIFICATE OF CORRECTION

Patent No. 3,962,420   Dated June 8, 1976

Inventor(s) Michael C. Seidel and Evan H. Crook

It is certified that error appears in the above-identified patent and that said Letters Patent are hereby corrected as shown below:

Col. 1, line 25 - "If" should read -- It --.

Col. 5, line 67 - should read: -- wherein R'' in formula II and

III is 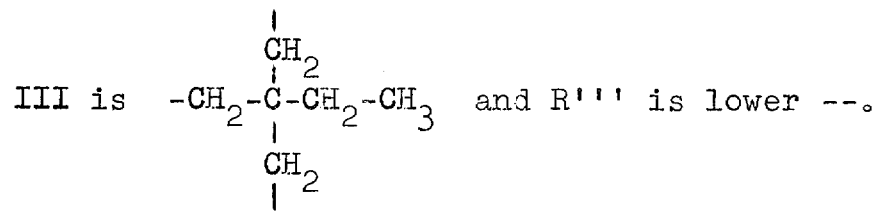 and R''' is lower --.

Col. 9, line 57 - should be dash (-) between word starch and magnesium.

Signed and Sealed this

Ninth Day of November 1976

[SEAL]

Attest:

RUTH C. MASON
*Attesting Officer*

C. MARSHALL DANN
*Commissioner of Patents and Trademarks*